(12) United States Patent
Liang et al.

(10) Patent No.: US 10,076,443 B2
(45) Date of Patent: Sep. 18, 2018

(54) PENETRATING CANALOPLASTY FOR TREATING ANGLE-CLOSURE GLAUCOMA

(71) Applicant: WENZHOU MEDICAL UNIVERSITY, Wenzhou, Zhejiang (CN)

(72) Inventors: Yuanbo Liang, Wenzhou (CN); Cheng Hu, Wenzhou (CN); Na Liao, Wenzhou (CN); Shaodan Zhang, Wenzhou (CN)

(73) Assignee: WENZHOU MEDICAL UNIVERSITY, Wenzhou, Zhejiang (CN)

( * ) Notice: Subject to any disclaimer, the term of this patent is extended or adjusted under 35 U.S.C. 154(b) by 81 days.

(21) Appl. No.: 15/362,478

(22) Filed: Nov. 28, 2016

(65) Prior Publication Data

US 2018/0147088 A1 May 31, 2018

(51) Int. Cl.
*A61F 9/007* (2006.01)
*A61B 17/02* (2006.01)
*A61F 9/00* (2006.01)

(52) U.S. Cl.
CPC ...... *A61F 9/00781* (2013.01); *A61B 17/0231* (2013.01); *A61F 9/0017* (2013.01); *A61F 9/00736* (2013.01)

(58) Field of Classification Search
CPC ............ A61F 9/00781; A61F 9/0017; A61F 2009/00891; A61F 9/00736
See application file for complete search history.

*Primary Examiner* — Emily Schmidt
(74) *Attorney, Agent, or Firm* — Christensen, Fonder, Dardi & Herbert PLLC

(57) ABSTRACT

A penetrating canaloplasty for treating angle-closure glaucoma that retains the advantages of canaloplasty, namely, internal drainage and non-bleb-dependence; the sclera is tightly sutured so as to avoid ocular hypotension and shallow anterior chamber complications; bleb-related complications such as postoperative infection and dry eye are avoided; since an inner wall of the Schlemm's canal is resected, it is possible to improve long-term success rates; indications are widened, including angle-closure glaucoma and all of glaucoma patients applicable to trabeculectomy. Traditional trabeculectomy forms blebs through outer filtering to reduce intraocular pressure, and the existence of blebs can influence postoperative living quality of patients. In contrast, the penetrating canaloplasty is a non-filtering operation, does not form blebs after operation, does not damage immunologic and physiologic structure of ocular surfaces and slightly influences quality of the tear film, and patients may gain relatively good ocular surface environment after operation.

6 Claims, 2 Drawing Sheets

PENETRATING CANALOPLASTY FOR TREATING ANGLE-CLOSURE GLAUCOMA

TECHNICAL FIELD

The present invention particularly relates to the technical field of ophthalmic surgery, particularly to penetrating canaloplasty for treating glaucoma, especially angle-closure glaucoma.

BACKGROUND

Glaucoma is an optic nerve damage disease caused by pathological intraocular hypertension, and control of intraocular pressure has become a main means for treatment of glaucoma. Although anti-glaucoma drugs and laser techniques provide techniques and possibility for control of intraocular pressure, due to specificity of the disease, a significant part of glaucoma patients have to receive operative treatment in the end. At present, the mainstream surgery for glaucoma is trabeculectomy, complications of the glaucoma filtering surgery can't be avoided, such as postoperative hypotony, shallow anterior chamber, choroidal detachment and cystoid macular edema as well as problems like bleb scarring may lead to operation failure.

Seeking a safe and reliable operation method has always been a trend for ophthalmologists.

Since the non-penetrating glaucoma operation has been introduced to China in 1990s, experts have made a lot of researches. Canaloplasty is a new non-filtering glaucoma surgery appearing in recent years, referring to implanting a suture into Schlemm's canal through a special microcatheter to expand Schlemm's canal and reestablish the natural passway of aqueous humor, thereby reducing intraocular pressure to treat glaucoma. Without formation of conjunctival blebs, avoiding a series of complications such as dry eye, discomfortable ocular surface, change of immunoarchitecture and prone infection caused by formation of conjunctival blebs, drawing more and more attention from ophthalmologists. Clinical application indicates that it has good and safe intraocular pressure reducing effect. However, current researches show that canaloplasty is only applicable to open-angle glaucoma. For angle-closure glaucoma, canaloplasty becomes an operative contraindication and cannot be widely applied in clinic due to synechia and blocking of iris in anterior chamber angle.

SUMMARY

We developed a new procedure, combining the canaloplasty with trabeculectomy, iridectomy, but tightly closed the scleral flap. With this procedure, the humor aqueous are drained from anterior chamber through internal trabeculectomy to subsclearal flap, then go through the suture-expanded osteum of schlemm canal. Theoretically, it can to restore the physiological pathway of aqueous flow, avoiding a bleb-dependent outflow pathway. Since canaloplasty is usually categorized into non-penetrating surgery in open angle glaucoma, so we called this procedure PENETRATING CANALOPLASTY.

The technical solution adopted by the present invention is a penetrating canaloplasty for treating angle-closure glaucoma comprising the following steps of:

(1) Surgery starts with a fornix-based conjunctival flap and a 4×4 mm superficial scleral flap, similar to that performed in deep sclerectomy. A deep scleral flap is then sculpted, and Schlemm's canal is opened and deroofed by the removal of the external wall, which is performed after paracentesis in order to lower the IOP, thus reducing the risk of perforation of the trabeculodescemet membrane. The deep scleral flap (2×2 mm) is removed and the two ostia of the canal are dilated with high molecular weight hyaluronic acid (Healon GV), similarly to a viscocanalostomy.

(2) The microcatheter, which is connected to a laser flickering red light source for an easy identification of the distal tip through the sclera, is then inserted and pushed forward within Schlemm's canal for the entire 360 degrees until it comes out of the other end of the of the canal opening. A single or double 10-0 prolene suture is then tied to the distal tip and the microcatheter is withdrawn and pulled back through the canal in the opposite direction. A small amount of viscoelastic agent is delivered in Schlemm's canal at every two clock hours while the catheter is withdrawn with the aid of a special screw-driven syringe. The suture is then knotted under tension in order to inwardly distend the trabecular meshwork.

(3) Then cut off the deep trabecular tissue (2×2 mm) at Schlemm canal and forward, and the respective iris root was cut.

(4) Finally the superficial scleral flap is tightly sutured with 10-0 prolene sutures to ensure a watertight closure preventing any bleb formation, 2 or 4 interrupted sutures. The conjunctival flap is then sutured with 10-0 prolene sutures to peripheral cornea.

The tail end of the microcatheter body where the luminescent head of the optical fiber is provided is 250 μm in diameter.

The syringe is a spiral syringe.

The present invention has the beneficial effects that a penetrating canaloplasty for treating glaucoma, especially for angle-closure glaucoma, which retains the advantages of canaloplasty, namely, internal drainage and non-bleb dependence; sclera is tightly sutured so as to avoid ocular hypotension and shallow anterior chamber complications; bleb-related complications such as postoperative infection and dry eye are avoided; for the reason that the inner wall of Schlemm's canal is resected, it is possible to improve long-term success rate and widen indications to include angle-closure glaucoma and all of glaucoma patients applicable to trabeculectomy. The traditional trabeculectomy forms blebs through outer filtering to reduce intraocular pressure, existence of blebs would influence postoperative living quality of patients and it is easy to generate bleb infection as well as dry eye and other discomforts caused by damage of quality of a tear film; whereas, the penetrating canaloplasty is a non-filtering operation, does not form blebs after operation, does not damage immunologic and physiologic structure of ocular surface and slightly influences the quality of the tear film, and patients may gain relatively good ocular surface environment after operation. This operation will expand indications of canaloplasty, promotes the clinical application of canaloplasty and provides a new ideas and suggestions for glaucoma, especially for angle-closure glaucoma.

Figure 1:
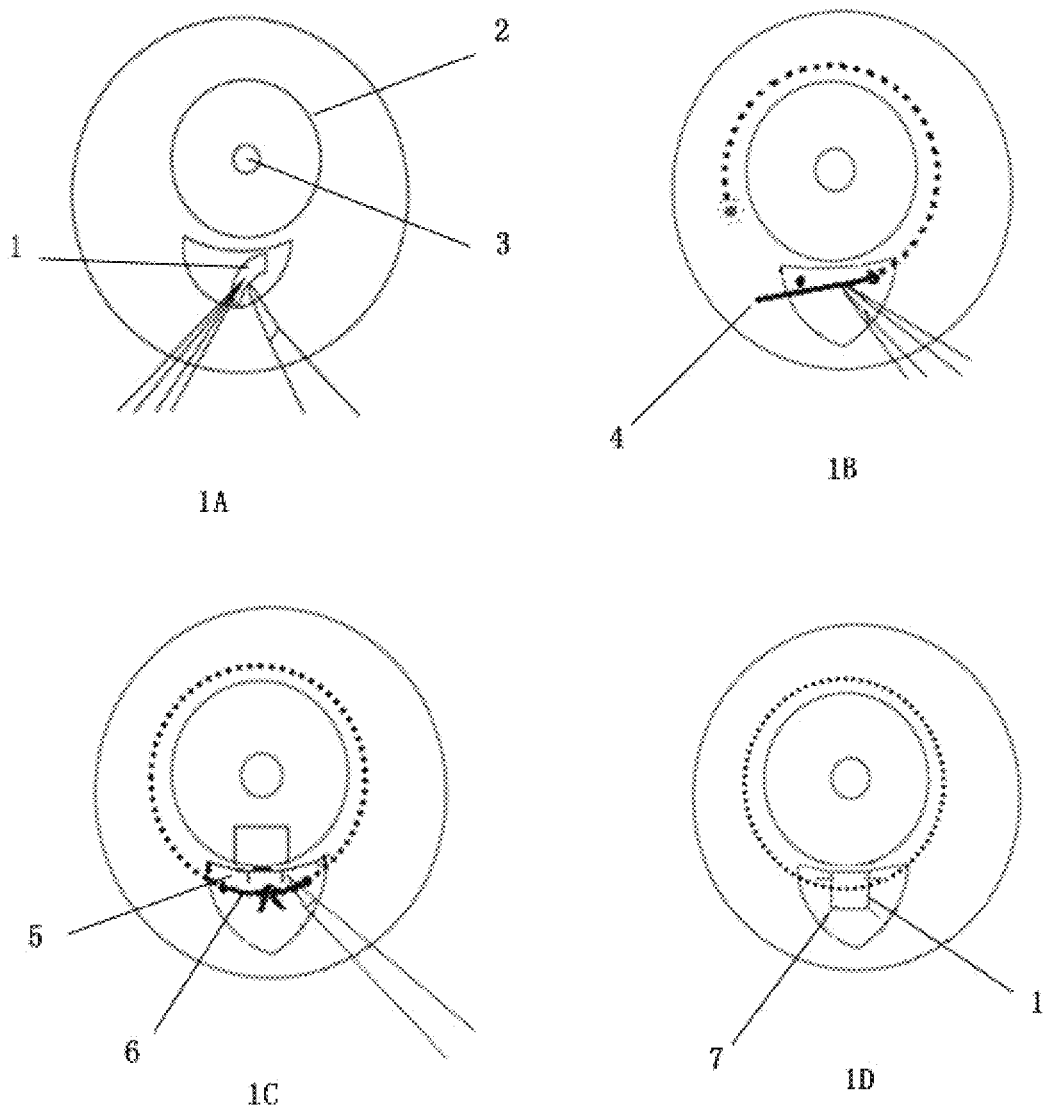
FIG. 1 is a flowchart diagram of penetrating canaloplasty implementing the present invention.
Figure 2:
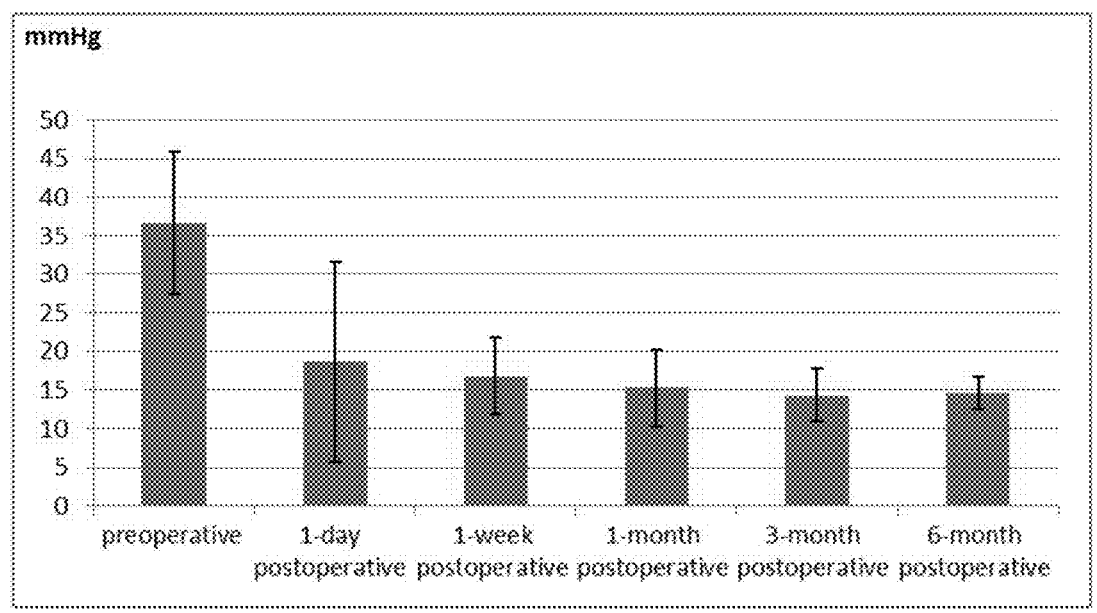
FIG. 2 is a statistic graph of operative effects of 9 cases of penetrating canaloplasty for angle-closure glaucoma at early stage.

Wherein, in FIG. 1, 1A illustrates excision of sclera flap and deep sclera, 1B illustrates completion of microcatheter probing, viscocanal and suture expansion, 1C illustrates combination of trabeculectomy, and 1D illustrates tight suturing of sclera flap; and 1—sclera flap, 2—cornea, 3—pupil, 4—microcatheter, 5—trabecular meshwork, 6—10-0 prolene suture, 7—suture.

DETAILED DESCRIPTION

In the penetrating canaloplasty, the operation adopts a microcatheter having a diameter of 200 µm, the tail end of the microcatheter is 250 µm in diameter so as to prevent tissues from being damaged when the microcatheter is inserted, an optical fiber is arranged inside the microcatheter, the luminescent head can be observed through sclera when the microcatheter is inserted into Schlemm's canal so as to confirm the position of the microcatheter. The microcatheter is connected to an eye microscopic operation device and is also connected with a syringe device, and a spiral syringe is capable of controlling the volume of injected liquid more precisely than a traditional driven syringe.

Routine disinfection and draping is performed on an operative eye, an eye speculum is placed, iodophor solution is diluted to wash a conjunctival sac, traction suture and fixation of superior rectus is performed after 0.4 ml of 2% lidocaine is used for topical subconjunctival infiltration anesthesia on the operative eye, an edge around the bulbar conjunctiva from the 11 o'clock position to the 1 o'clock position is incised, a shallow scleral flap that uses the limbus cornea as a fundus with a size of 4*4 mm and a thickness of ⅓ scleral thickness is made with the 12 o'clock position as a center, and a deep scleral flap with a size of 3*3 mm and a thickness of ⅔ scleral is further made under the shallow scleral flap, stripping is performed toward the direction of cornea to find Schlemm's canal, the outer wall of Schlemm's canal is incised, macromolecular hyaluronic acid is injected into Schlemm's canal at its two ends using a 30 G syringe needle so that the microcatheter can easily pass through an opening, a part of the posterior elastic layer of cornea is further forwardly exposed, a Descemet's membrane window is made and the deep scleral flap is excised. An anterior chamber paracentesis is performed parallel to the direction of the iris at 1.0 mm inside the limbus cornea at the 9 or 3 o'clock position, the rear edge of the paracentesis opening is slightly pressed, a proper amount of aqueous humor is discharged to reduce intraocular pressure, and the microcatheter is inserted into a broken end of Schlemm's canal after performing pressure reduction and paracentesis on anterior chamber and advances 360 degrees along Schlemm's canal until penetrating out of a broken end at an opposite side. After double-strand 10-0 polypropylene sutures are ligated at a tail end of the microcatheter, the microcatheter is retracted, and macromolecular sodium hyaluronate is injected while retracting, wherein each time the microcatheter is retracted by n/6 radian, a syringe connected with a viscoelastic agent injects 150 µl viscoelastic agent into Schlemm's canal to expand Schlemm's canal, after the microcatheter is completely retracted, the suture is left in Schlemm's canal, and after the sufficient expansion of Schlemm's canal is ensured, the double-strand sutures are respectively ligated. Then, deep trabecular tissue between Schlemm's canal and cornea is removed by 1.0 mm*1.5 mm using a scleral punch, corresponding iris root tissue is wiped out, scleral flap is hermetically sutured with 4 stitches using 10-0 polypropylene suture, balanced salt solution is injected into an anterior chamber paracentesis opening for observation by which watertight suturing can be confirmed if there is no leaking, and after the intraocular pressure is recovered to be normal, the conjunctival flap is sutured with 2 stitches using 10-0 polypropylene suture. Anti-inflammatory drugs are administered to the patient after operation, intraocular pressure and eye anterior segment response are monitored, and pressurized bandaging is performed on the single eye after the canaloplasty operation is finished.

The penetrating canaloplasty, which combining the canaloplasty with trabeculectomy, iridectomy, but tightly closed the scleral flap. With this procedure, the humor aqueous are drained from anterior chamber through internal trabeculectomy to subsclearal flap, then go through the suture-expanded osteum of schlemm canal. Theoretically, it can to restore the physiological pathway of aqueous flow, avoiding a bleb-dependent outflow pathway. Observation on of penetrating canaloplasty for 9 cases of angle-closure glaucoma patients at early stage finds that a good effect has been gained, at present, mean follow-up has already been performed for 6 months, the longest follow-up time is 12 months, mean chamber angle adhesion and closure range of 9 cases of angle-closure glaucoma patients is 330±47 degrees, mean fundus optic nerve head cup/disc ratio is 0.73±0.16, Humphrey visual field (24-2) indicates that mean defection (MD) is −23.31±8.11 dB, mean preoperative intraocular pressure is 36.6±9.3 mmHg, and 3.6±0.9 types of glaucoma drugs are used on average. For the 9 cases all receiving penetrating canaloplasty, mean intraocular pressure is 14.7±2.1 mmHg in 6 months after operation, and 0.1±0.3 types of glaucoma drugs are used on average. Tightly suturing sclera can achieve a state of no blebs after operation, and postoperative complications are greatly reduced as compared with that of trabeculectomy, proving that this operation method is effective and practicable for angle-closure glaucoma patients.

The penetrating canaloplasty provided by the present invention breaks through a fixed thinking mode of "non-penetrating", forms a new glaucoma operation method combined with a traditional trabeculectomy, and has the following advantages: 1. Advantages of canaloplasty are retained, namely, internal drainage and non-bleb-dependence; 2. Sclera is tightly sutured so as to avoid ocular hypotension related shallow anterior chamber and other complications; 3. Bleb-related complications such as postoperative infection and dry eye are avoided; 4. Since the inner wall of Schlemm's canal in the operated area is resected, the aqueous can pass through the window into the schlemm canal, it is irrelevant to the resistance of trabecular meshwork, therefor, it is possible to improve long-term success rate; 5. Indications are widened, including angle-closure glaucoma and all of glaucoma patients applicable to trabeculectomy. The traditional trabeculectomy forms blebs via outer filtering to reduce intraocular pressure, and the existence of blebs can influence postoperative living quality of patients as it is easy to generate bleb infection as well as dry eye and other discomforts generated by damage of quality of a tear film; in contrast, the penetrating canaloplasty is a not-filtering operation, does not form blebs after operation, does not damage immunologic and physiological structure of ocular surface and slightly influences the quality of the tear film, and patients may gain relatively good ocular surface environment after operation; this operation will expand the indications of canaloplasty, promotes the clinical application of canaloplasty and provides a new ideas and suggestions for angle-closure glaucoma.

The above description is only a preferred embodiment of the present invention, the protection scope of the present invention is not merely limited to the above embodiments, any technical solutions belonging to the ideas of the present invention fall within the protection scope of the present invention. It should be noted that for those of ordinary skill in the prior art, some improvements and embellishments should be considered as in the protection scope of the present invention without departing from the principle of the present invention.

The invention claimed is:

1. A penetrating canaloplasty for treating angle-closure glaucoma, characterized by comprising the following steps of:
   (1) performing conventional disinfection and draping on an operative eye, placing an eye speculum, washing a conjunctival sac, performing traction suture and fixation on a superior rectus after performing topical subconjunctival infiltration anesthesia on the operative eye, incising an edge around a bulbar conjunctiva from an 11 o'clock position to a 1 o'clock position according to clock positions, making a shallow scleral flap with a thickness of ⅓ scleral thickness that uses a corneal limbus as a fundus with a 12 o'clock position as a center, and further making a deep scleral flap with a thickness of ⅔ scleral thickness under the shallow scleral flap; stripping in a direction toward a cornea to find Schlemm's canal and incising an outer wall of the Schlemm's canal, injecting macromolecular hyaluronic acid into the Schlemm's canal at two ends of the Schlemm's canal, further forwardly exposing a part of a posterior elastic layer of the cornea, making a Descemet's membrane window and excising the deep scleral flap, performing anterior chamber paracentesis at a position 1.0 mm inside the limbus cornea at a 9 or 3 o'clock position parallel to a direction toward an iris, slightly pressing a rear edge of a paracentesis opening, discharging aqueous humor to reduce intraocular pressure, inserting a microcatheter into a broken end of the Schlemm's canal after performing pressure reduction and paracentesis on an anterior chamber, advancing 360 degrees along the Schlemm's canal until penetrating out of a broken end at an opposite side;
   (2) after ligating an ophthalmologic operation suture at a tail end of the microcatheter, retracting the microcatheter, and injecting macromolecular sodium hyaluronate while retracting, wherein each time the microcatheter is retracted by $\pi/6$ radian, a syringe connected with a viscoelastic agent injects the viscoelastic agent into the Schlemm's canal to expand the Schlemm's canal, after the microcatheter is completely retracted, the ophthalmologic operation suture is left in the Schlemm's canal, and after sufficient expansion of the Schlemm's canal is confirmed, two ends of the ophthalmologic operation suture are respectively ligated; and
   (3) then, removing deep trabecular tissues between the Schlemm's canal and the cornea using a scleral punch and wiping out corresponding iris root tissue, hermetically suturing the scleral flap using the ophthalmologic operation suture, injecting balanced salt solution into an anterior chamber paracentesis opening for observation by which watertight suturing can be confirmed if there is no leaking, after the intraocular pressure is recovered to be normal, suturing the conjunctival flap using the ophthalmologic operation suture, administering to a patient anti-inflammatory drugs after the canaloplasty, monitoring intraocular pressure and anterior segment response, and performing pressurized bandaging on the single eye after the canaloplasty is finished.

2. The penetrating canaloplasty for treating angle-closure glaucoma according to claim 1, characterized in that the microcatheter comprises a microcatheter body having a diameter of 200 pm, an optical fiber is arranged inside the microcatheter body, a head of the optical fiber at the tail end of the microcatheter body is luminescent, the luminescent head can be observed through the sclera when the microcatheter is inserted into the Schlemm's canal so as to confirm a position of the microcatheter, and the optical fiber is hollow to inject the viscoelastic agent thereto.

3. The penetrating canaloplasty for treating angle-closure glaucoma according to claim 2, characterized in that the tail end of the microcatheter body where the luminescent head of the optical fiber is provided is 250 μm in diameter.

4. The penetrating canaloplasty for treating angle-closure glaucoma according to claim 1, characterized in that the syringe is a spiral syringe.

5. The penetrating canaloplasty for treating angle-closure glaucoma according to claim 1, characterized in that the ophthalmologic operation suture is a 10-0 polypropylene suture.

6. The penetrating canaloplasty for treating angle-closure glaucoma according to claim 1, characterized in that an injection amount of the viscoelastic agent is 150 μL.

* * * * *